(12) United States Patent
Graupner

(10) Patent No.: US 6,763,972 B2
(45) Date of Patent: Jul. 20, 2004

(54) DISPENSER FOR THIN KNIVES, IN PARTICULAR FOR THIN REPLACEABLE MICROTOME KNIVES

(75) Inventor: Dag Graupner, Eppelheim (DE)

(73) Assignee: Leica Microsystems Nussloch GmbH, Nussloch (DE)

( * ) Notice: Subject to any disclaimer, the term of this patent is extended or adjusted under 35 U.S.C. 154(b) by 172 days.

(21) Appl. No.: 10/192,546

(22) Filed: Jul. 10, 2002

(65) Prior Publication Data

US 2003/0015545 A1 Jan. 23, 2003

(30) Foreign Application Priority Data

Jul. 11, 2001 (DE) .................................... 201 11 599 U

(51) Int. Cl.⁷ ............................................... B65H 1/08
(52) U.S. Cl. ..................................... 221/232; 221/268
(58) Field of Search ............................... 221/232, 268, 221/256, 269, 270, 271, 276, 283, 255; 206/354, 355, 39.5

(56) References Cited

U.S. PATENT DOCUMENTS 3,542,245 A * 11/1970 Braginetz ................... 221/232
3,827,597 A    8/1974 Braginetz
4,700,600 A   10/1987 Pickett
5,409,133 A *  4/1995 Gringer ...................... 221/102

FOREIGN PATENT DOCUMENTS

| DE | 12 47 571 A   | 8/1967 |
| DE | 28 52 373 C2  | 6/1979 |
| DE | 28 52 373 A   | 6/1980 |
| DE | 30 17 751 A   | 7/1981 |
| EP | 0 796 803 A   | 9/1997 |

* cited by examiner

Primary Examiner—Kenneth Noland
(74) Attorney, Agent, or Firm—Hodgson Russ LLP

(57) ABSTRACT

A dispenser for thin replaceable knives, for example microtome knives, comprises a housing (3) for the reception of multiple knives (2) arranged in a stack (5). The housing includes a cover (7) and a longitudinal wall (10) adjacent to the housing cover (7) through which a dispensing opening (9) is provided. A spring (6) is arranged for biasing the knife stack (5) against the inside of the housing cover (7), and a slider (8) is provided to travel within a groove (16) on the outside of the housing cover (7) for engaging an individual knife (2) and pivoting the individual knife such that at least a portion of the knife protrudes out of the housing (3), wherein a knife edge (11) along the protruding knife portion faces back in the direction of the opening (9).

11 Claims, 3 Drawing Sheets

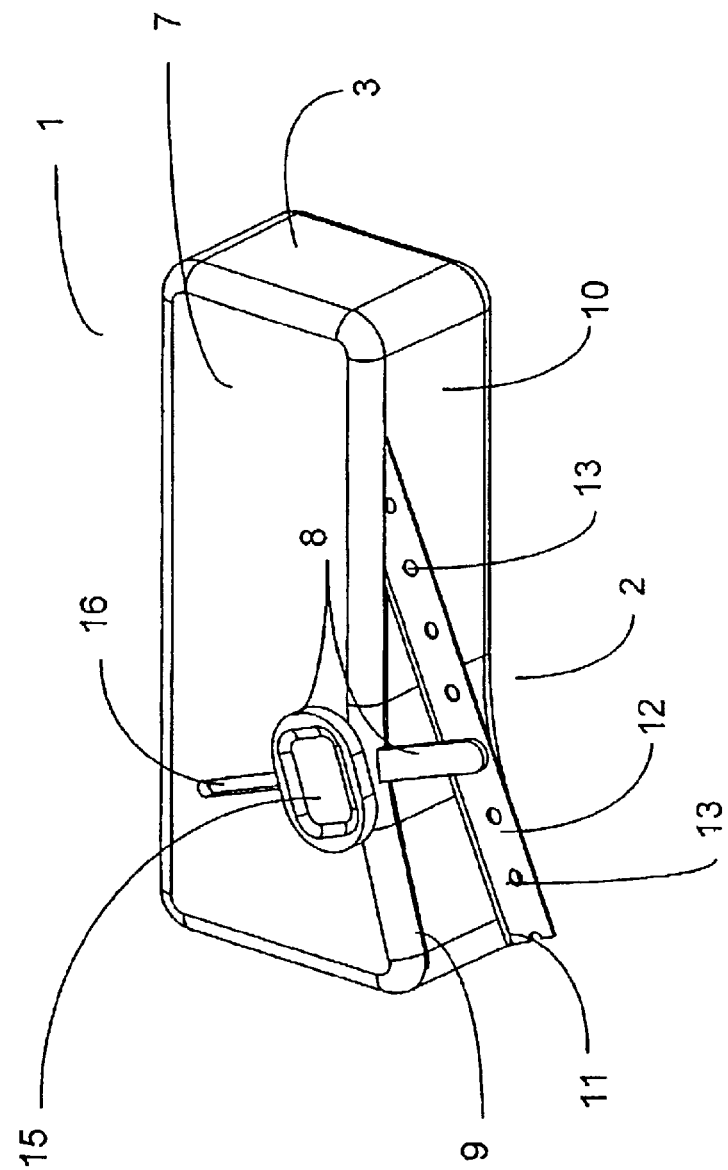

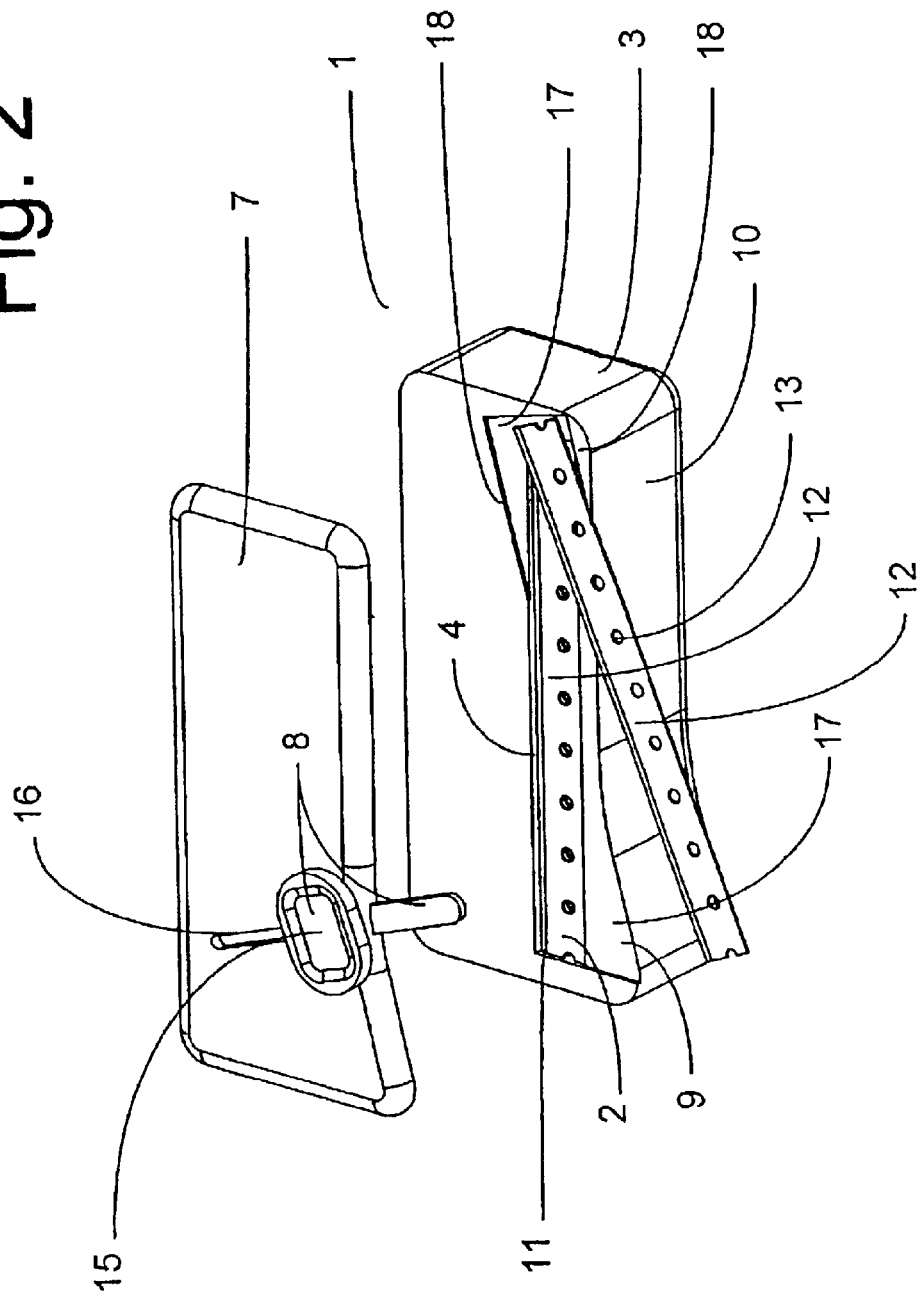

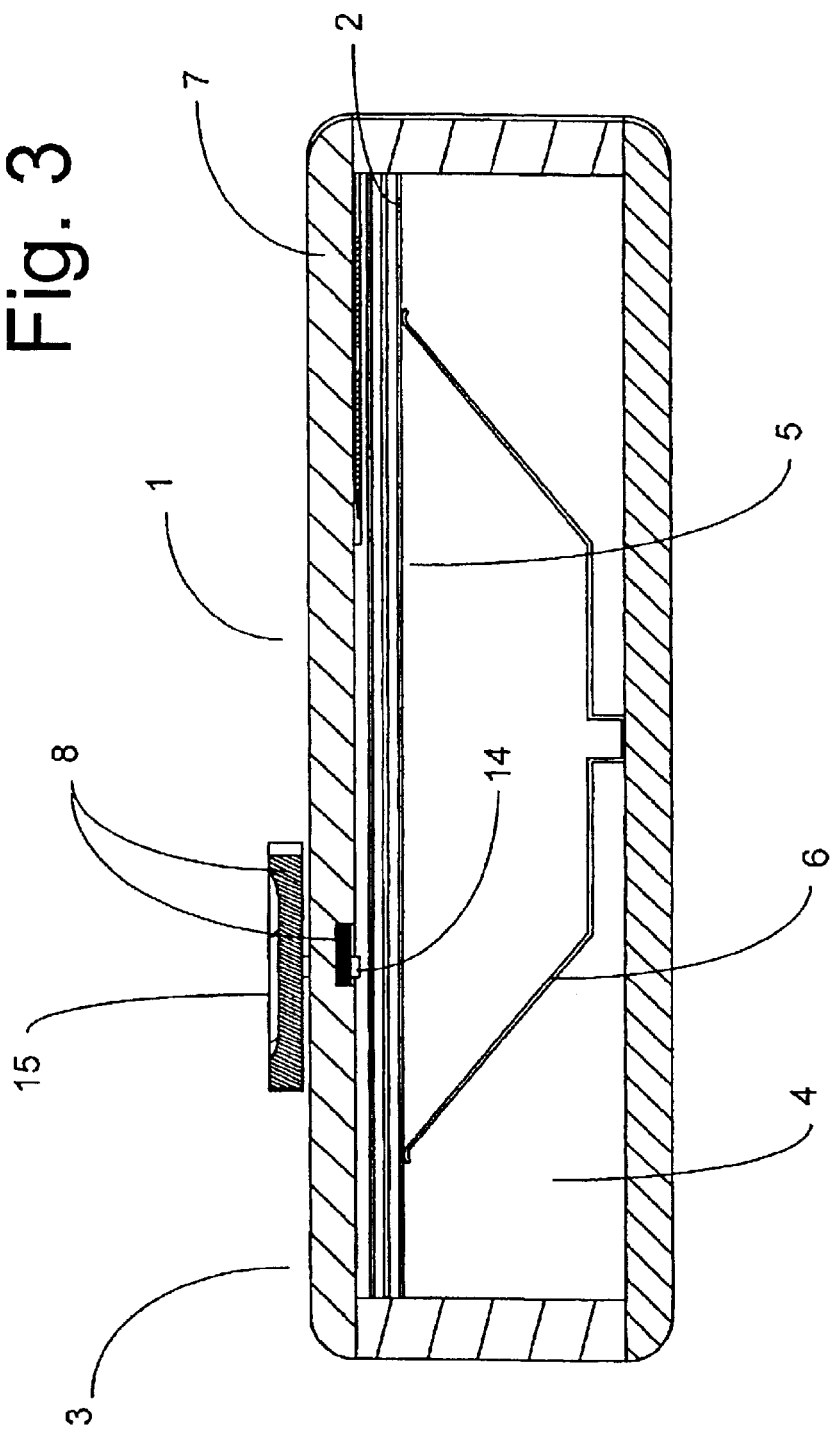

DISPENSER FOR THIN KNIVES, IN PARTICULAR FOR THIN REPLACEABLE MICROTOME KNIVES

CROSS REFERENCE TO RELATED APPLICATIONS

This application claims priority of the German utility model application 201 11 599.9 filed Jul. 11, 2001 which is incorporated by reference herein.

FIELD OF THE INVENTION

The invention concerns a dispenser for thin knives, in particular for thin replaceable microtome knives.

BACKGROUND OF THE INVENTION

Thin knives, in particular thin replaceable microtome knives, are used as so-called "disposable blades" for sectioning preparations with a microtome for subsequent microscopic examination. The replaceable microtome knives are received by special knife holders and clamped therein. For sectioning the preparation, the entire knife holder is received by a holding apparatus on the microtome.

The replaceable microtome knives have only a limited service life. As cutting performance declines, the knives must be replaced. The replaceable microtome knives are offered commercially in so-called "dispensers"; in these, several knives are arranged one above another in a housing and can be removed therefrom individually.

A dispenser of this kind for thin replaceable microtome knives is depicted and described, together with a knife holder, in DE 28 52 373 C2. The dispenser is characterized in that in a closed parallelepipedal housing, a stack of individual replaceable microtome blades arranged one above another is pressed by a leaf spring against the cover of the housing. Provided in the cover is a slider, with which one individual knife can be slid out through a slot arranged in the end wall of the parallelepipedal housing.

The knife can be slid directly into the knife holder by way of a stud shaped onto the dispenser and a corresponding blind hole in the knife holder. This requires, however, that the knife holder be accessible from the side. In addition, this dispenser can be placed only onto a special knife holder. If a special knife holder is not used, the blades must be removed by hand after being slid out of the knife holder, and inserted manually into the knife holder. Since the knife blade projects out of the dispenser in entirely unprotected fashion after being slid out, an increased risk of injury exists here.

SUMMARY OF THE INVENTION

It is therefore the object of the present invention to improve a dispenser of this kind for replaceable microtome knives in such a way that the risk of injury upon manual removal of the knife is minimized.

According to the present invention, this object is achieved by the characterizing features of claim 1. Advantageous developments are the subject matter of the dependent claims.

The invention is characterized in that the dispenser for thin replaceable microtome knives has, in one of the two longitudinal walls of the housing, an opening which is dimensioned in such a way that the knife is slid out of the housing along its longitudinal extension in a pivoting motion of the slider. In the process, the knife edge always faces in the direction of the opening, so that the knife is grasped at its non-hazardous narrow back surface and can be placed into a knife holder.

In an embodiment of the invention, provision is made for the back of the replaceable microtome knife to comprise at least one hole or at least one depression for a snap-in stud. It has proven advantageous, however, if the knife back comprises a continuous series of holes and/or depressions arranged next to one another. During manufacture of the knife, an "endless" steel strip can be guided in planar fashion over a grinder in order to grind the knife edge, and can then be cut off to the desired knife length.

Provision is made for the slider to comprise a snap-in stud for engagement into the hole or depression on the knife. An actuation of the slider causes the knife to be slid out.

For more reliable handling, the slider is equipped with a recess that results in better finger contact with the slider.

In a further embodiment of the invention, the slider is guided in a groove in the cover of the housing, the groove being arranged obliquely with respect to the knife edge. The result of this is that one end of the knife is pivoted out of the housing and the other end of the knife remains in the housing. Provision can also be made for the slider groove to be arranged in the housing such that the slider engages the knife at a location spaced from the center of the knife such that one end of the knife is pivoted out of the housing and the other end of the knife remains in the housing.

In a further embodiment of the invention, the gap in the housing for pivoting the blade out has associated with it a support surface, located lower down, for the blade. This has the advantage that the blade is securely guided while being pivoted out, and moreover can be held securely against the support after being partially pivoted out.

Provision is furthermore made for the support surface to have associated with it a stop for limiting the movement of the knife that can be pivoted out. This prevents the knife from shifting unintentionally after being pivoted out, since on the one side it is guided by the slider and on the other side it rests on the support surface against a stop.

BRIEF DESCRIPTION OF THE DRAWINGS

The invention is depicted and explained in more detail, in an exemplary embodiment, with reference to the schematic drawings in which:

FIG. 1 is a view of the dispenser with a replaceable microtome knife pivoted out;

FIG. 2 is a view of the dispenser with the cover removed; and

FIG. 3 is a section through the dispenser.

DETAILED DESCRIPTION OF THE INVENTION

FIG. 1 shows a view of a dispenser 1 having a housing 3, a housing cover 7, and an opening 9 provided in a longitudinal wall 10 of housing 3. Arranged in housing cover 7 is a groove 16 for guidance of a slider 8 that has a recess 15 for better handling. By way of slider 8, a replaceable microtome knife 2 is pivoted out of the interior of housing 3.

Replaceable microtome knife 2 has a knife edge 11 that, when knife 2 is in the pivoted-out state, faces toward longitudinal wall 10 of housing 3 and toward opening 9. Knife 2 comprises, in its knife back 12, holes 13 arranged next to one another and spaced evenly apart from one another. Snap-in stud 14 (not depicted here) of slider 8 engages into one of said holes 13.

FIG. 2 shows a view of dispenser 1 with housing cover 7 removed. A knife stack receptacle 4, for multiple knifes 2 arranged one above another, is provided in housing 3. A support surface 17 for guidance and support of knife 2 that is to be pivoted out is provided at opening 9. Support surface 17 has, at its end opposite slider 8, a stop 18 to limit the movement of knife 2 that has been pivoted out.

FIG. 3 shows a section through housing 3, with housing cover 7 in which slider 8 is guided. Slider 8 comprises a shaped-on snap-in stud 14 for engagement into the holes (not depicted here) of replaceable microtome knife 2.

The interior of housing 3 comprises knife stack receptacle 4, in which a knife stack 5 of individual knives 2 arranged one above another is provided. Knife stack 5 is nonpositively connected to a spring 6, and is pressed by the latter against housing cover 7.

Snap-in stud 14 engages into a hole 13 of knife 2. Using slider 8, knife 2 is manually pivoted out against stop 18. After the removal of knife 2, slider 8 can be pushed back into its starting position. Snap-in stud 14 then engages into a hole 13 of knife 2 that is now at the top.

The invention is not limited to the exemplary embodiment described; rather, in addition to the replaceable microtome knifes described, carpet knife blades, razor blades, cutter knife blades, or similar thin blades can also be used.

PARTS LIST

1 Dispenser
2 Replaceable microtome knife
3 Housing
4 Knife stack receptacle
5 Knife stack
6 Spring
7 Housing cover
8 Slider
9 Opening
10 Longitudinal wall of 3
11 Knife edge
12 Knife back
13 Hole
14 Snap-in stud
15 Recess
16 Groove
17 Support surface
18 Stop

What is claimed is:

1. A dispenser (1) for thin replaceable knives, said dispenser comprising:
    a housing (3) for the reception of multiple knives arranged in a stack (5), said housing including a cover(7) and a longitudinal wall (10) adjacent to said housing cover (7), said wall (10) having an opening (9) therethrough;
    a spring (6) arranged for pressing said knife stack (5) against said housing cover (7); and
    a slider (8) for engaging an individual knife (2) and sliding said individual knife out through an opening (9) in the wall of the housing (3);
    wherein said individual knife (2) is pivoted by said slider (3) such that at least a portion of said individual knife (2) extends out of said housing (3) and a knife edge (11) along said portion faces in the direction of said opening (9).

2. The dispenser for thin knives as defined in claim 1, wherein said slider (8) comprises a stud (14) for engagement into a hole (13) in said individual knife (2).

3. The dispenser for thin knives as defined in claim 1, wherein said slider (8) comprises a recess (15) for more reliable handling.

4. The dispenser for thin knives as defined in claim 1, wherein said cover (7) includes a groove (16) and said slider (8) is guided in said groove (16).

5. The dispenser for thin knives as defined in claim 4, wherein said groove (16) is arranged obliquely with respect to said knife edge (11).

6. The dispenser for thin knives as defined in claim 4, wherein said groove (16) is arranged in said housing cover (7) such that said slider (8) engages said individual knife (2) at a location spaced from a longitudinal center of said individual knife (2).

7. The dispenser for thin knives as defined in claim 5, wherein said groove (16) is arranged in said housing cover (7) such that said slider (8) engages said individual knife (2) at a location spaced from a longitudinal center of said individual knife (2).

8. The dispenser (1) for thin knives as defined in claim 1, further comprising a support surface associated with said opening (9) and located under said individual knife (2).

9. The dispenser for thin knives as defined in claim 8, wherein a portion of said support surface (17) is bounded by a stop (18) for limiting the movement of said individual knife (2).

10. In combination:
    a plurality of thin replaceable knives (2) each including a hole (13) therein; and
    a dispenser (1) for holding said plurality of thin replaceable knives and selectively dispensing an individual knife (2) taken from said plurality of thin replaceable knives, said dispenser comprising:
        a housing (3) for the reception of multiple knives (2) arranged in a stack (5), said housing including a cover(7) and a longitudinal wall (10) adjacent to said housing cover (7), said wall (10) having an opening (9) therethrough;
        a spring (6) arranged for pressing said knife stack (5) against said housing cover (7); and
        a slider (8) for engaging an individual knife (2) and sliding said individual knife out through an opening (9) in the wall of the housing (3);
        wherein said individual knife (2) is pivoted by said slider (3) such that at least a portion of said individual knife (2) extends out of said housing (3) and a knife edge (11) along said portion faces in the direction of said opening (9).

11. The combination as defined in claim 10, wherein said slider (8) comprises a snap-in stud (14) for engagement into said hole (13) of said individual knife (2).

* * * * *